US012582981B2

(12) United States Patent
Webster

(10) Patent No.: US 12,582,981 B2
(45) Date of Patent: Mar. 24, 2026

(54) FLUIDIC CHANNELS INCLUDING CONDUCTIVITY SENSOR AND METHODS OF USE THEREOF

(71) Applicant: Zomedica Biotechnologies LLC, Ann Arbor, MI (US)

(72) Inventor: James Russell Webster, Minnetonka, MN (US)

(73) Assignee: Zomedica Biotechnologies LLC, Ann Arbor, MI (US)

( * ) Notice: Subject to any disclaimer, the term of this patent is extended or adjusted under 35 U.S.C. 154(b) by 9 days.

(21) Appl. No.: 18/189,827

(22) Filed: Mar. 24, 2023

(65) Prior Publication Data

US 2023/0234045 A1     Jul. 27, 2023

Related U.S. Application Data

(62) Division of application No. 17/724,204, filed on Apr. 19, 2022, now Pat. No. 11,612,887, which is a
(Continued)

(51) Int. Cl.
B01L 3/00          (2006.01)
G01F 1/58          (2006.01)
(Continued)

(52) U.S. Cl.
CPC .............. B01L 3/502 (2013.01); G01F 1/584 (2013.01); G01N 27/08 (2013.01); G01N 33/49 (2013.01);
(Continued)

(58) Field of Classification Search
CPC ............. B01L 3/502; B01L 2200/0605; B01L 2200/14; B01L 2200/16; B01L 2300/0645;
(Continued)

(56) References Cited

U.S. PATENT DOCUMENTS

| | | |
|---|---|---|
| 4,547,735 A | 10/1985 | Kiesewetter et al. |
| 6,058,934 A | 5/2000 | Sullivan |

(Continued)

FOREIGN PATENT DOCUMENTS

| | | |
|---|---|---|
| CN | 104427929 A | 3/2015 |
| CN | 105452858 A | 3/2016 |

(Continued)

OTHER PUBLICATIONS

Burns et al., "An Integrated Nanoliter DNA Analysis Device", Science, vol. 282, Oct. 16, 1998, pp. 484-487.
(Continued)

*Primary Examiner* — Samuel P Siefke

(74) *Attorney, Agent, or Firm* — Standley Law Group LLP; Jeffrey S. Standley; Bryan P. Finneran

(57)          ABSTRACT

Devices that includes a first portion, the first portion including at least one fluid channel; a fluid actuator; an analysis sensor disposed within the fluid channel; a conductivity sensor disposed within the fluid channel; and an introducer; a second portion, the second portion comprising: at least one well, the well containing at least one material, wherein one of the first or second portion is moveable with respect to the other, wherein the introducer is configured to obtain at least a portion of the material from the at least one well and deliver it to the fluid channel, and wherein the fluid actuator is configured to move at least a portion of the material in the fluid channel.

5 Claims, 1 Drawing Sheet

Related U.S. Application Data division of application No. 16/120,224, filed on Sep. 1, 2018, now Pat. No. 11,344,878.

(60) Provisional application No. 62/694,621, filed on Jul. 6, 2018, provisional application No. 62/694,594, filed on Jul. 6, 2018, provisional application No. 62/694,599, filed on Jul. 6, 2018.

(51) Int. Cl.
G01N 27/08 (2006.01)
G01N 33/49 (2006.01)

(52) U.S. Cl.
CPC ... *B01L 2200/0605* (2013.01); *B01L 2200/14* (2013.01); *B01L 2200/16* (2013.01); *B01L 2300/0645* (2013.01); *B01L 2300/0663* (2013.01)

(58) Field of Classification Search
CPC ....... B01L 2300/0663; B01L 3/502715; B01L 3/0293; B01L 3/50855; B01L 2200/025; B01L 2200/0684; B01L 2300/044; B01L 2300/0672; B01L 2300/0829; B01L 3/5027; B01L 2300/0816; B01L 2300/0883; B01L 2300/161; B01L 2400/0487; G01F 1/584; G01N 27/08; G01N 33/49; G01N 29/02; G01N 29/022; G01N 29/036; G01N 29/222; G01N 33/487; G01N 33/54366; G01N 2291/0255; G01N 2291/0256; G01N 2291/0426; G01N 33/4875
See application file for complete search history.

(56) References Cited

U.S. PATENT DOCUMENTS

| | | | |
|---|---|---|---|
| 11,344,878 | B2 | 5/2022 | Webster |
| 11,541,385 | B2 | 1/2023 | Webster |
| 11,612,887 | B2 | 3/2023 | Webster |
| 2001/0049148 | A1 | 12/2001 | Wolk et al. |
| 2002/0015667 | A1 | 2/2002 | Chow |
| 2003/0203504 | A1 | 10/2003 | Hefti |
| 2008/0297169 | A1 | 12/2008 | Greenquist et al. |
| 2009/0084678 | A1 | 4/2009 | Joshi et al. |
| 2011/0201099 | A1* | 8/2011 | Anderson ......... G01N 1/10 422/68.1 |
| 2012/0258472 | A1 | 10/2012 | Roy et al. |
| 2012/0329144 | A1 | 12/2012 | Kwak et al. |
| 2014/0273265 | A1 | 9/2014 | Feingold et al. |
| 2016/0091506 | A1 | 3/2016 | Webster |
| 2016/0091511 | A1 | 3/2016 | Di Tullio et al. |
| 2016/0116444 | A1 | 4/2016 | Webster et al. |
| 2020/0011825 | A1 | 1/2020 | Webster |
| 2020/0011849 | A1 | 1/2020 | Webster |
| 2023/0133768 | A1 | 5/2023 | Webster |

FOREIGN PATENT DOCUMENTS

| | | | |
|---|---|---|---|
| GB | 2501128 | A | 10/2013 |
| JP | 2005-283163 | A | 10/2005 |
| JP | 2006-167706 | A | 6/2006 |
| JP | 2006-329899 | A | 12/2006 |
| JP | 2009-276275 | A | 11/2009 |
| WO | WO 2013/153406 | A1 | 10/2013 |
| WO | WO 2014/190295 | A2 | 11/2014 |
| WO | WO 2016/049557 | A1 | 3/2016 |
| WO | WO 2017/195038 | A1 | 11/2017 |
| WO | 2020/009896 | A1 | 1/2020 |
| WO | 2020/009897 | A1 | 1/2020 |

OTHER PUBLICATIONS

Sandberg et al., "Relation Between Blood Resistivity and Hematocrit in Fresh Human Fetal Blood", Pediatr. Res. 15, 1981, pp. 964-966.
Kim et al., "Improvement of the accuracy of continuous hematocrit measurement under various blood flow conditions" Appl. Phys. Lett. 104, 153508 (2014).
Kim et al., "Improvement of electrical blood hematocrit measurements under various plasma conditions using a novel hematocrit estimation parameter" Biosensors and Bioelectronics 35 (2012) 416-420.
Rothe et al., "Continuous measurement of conductivity of biological fluids" Journal of Applied Physiology vol. 23, No. 6, Dec. 1967.
Trebbels et al., "Capacitive on-line hematocrit sensor design based on Impedance Spectroscopy for use in hemodialysis machines" 31st Annual International Conference of the IEEE EMBS Minneapolis, Minnesota, USA, Sep. 2-6, 2009.
Jung et al., "Determination of hematocrit using on-line conductance cell," International Journal of Heat and Mass Transfer 55 (2012), pp. 1836-1843.
Zhbanov et al., "Electrochemical impedance spectroscopy of blood for sensitive detection of blood hematocrit, sedimentation and dielectric properties," Anal. Methods, 2017, 9, 3302-3313.
Teodorczyk et al., "Hematocrit compensation in electrochemical blood glucose monitoring systems," J. Diabetes Sci. Technol. Vol. 6, Issue 3, May 2012.
International Search Report and Written Opinion for PCT Application No. PCT/US2019/039465 dated Sep. 5, 2019, 9 pages.
International Preliminary Report on Patentability for PCT Application No. PCT/US2019/039465 dated Jan. 12, 2021, 8 pages.
International Search Report and Written Opinion for PCT Application No. PCT/US2019/039470 dated Sep. 17, 2019, 9 pages.
International Preliminary Report on Patentability for PCT Application No. PCT/US2019/039470 dated Jan. 12, 2021, 7 pages.
Extended European Search Report dated Feb. 28, 2022 from European application No. EP 19831195.3, 7 pages.
Extended European Search Report dated Feb. 28, 2022 from European application No. EP 19831197.9, 7 pages.
Office Action dated Mar. 31, 2023 from Chinese Application No. 201980045635.4, original and English translation, 10 pages.
Office Action dated Mar. 31, 2023 from Chinese Application No. 201980045868.4, original and English translation, 15 pages.
Office Action dated Apr. 11, 2023 from Japanese Application No. 2021-500195, original and English translation, 8 pages.
Office Action mailed May 16, 2023 for Japanese application No. 2021-500212, with English translation, 8 pages.

* cited by examiner

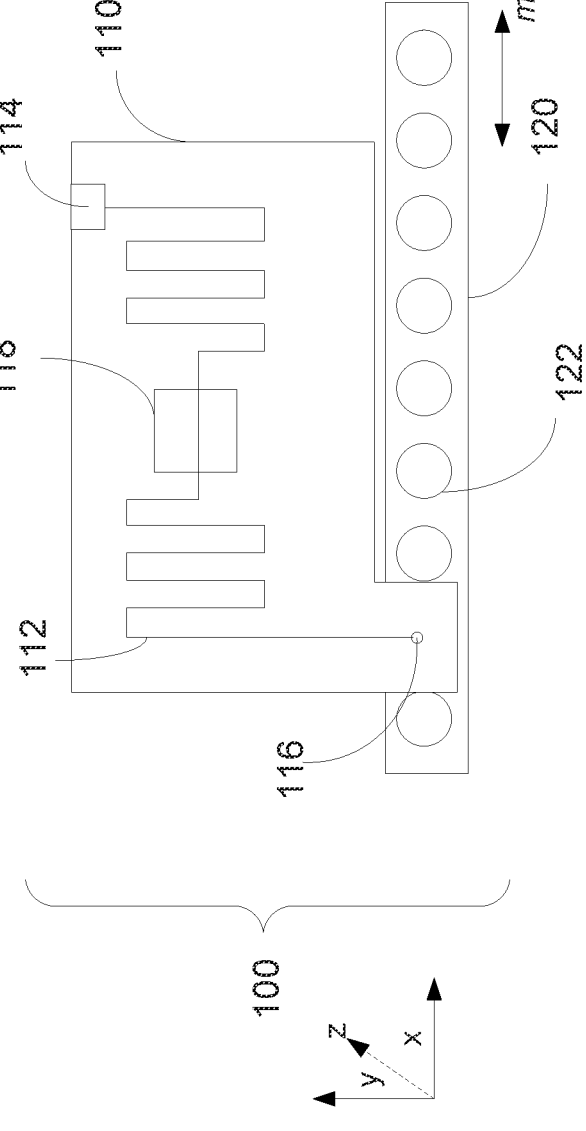

FLUIDIC CHANNELS INCLUDING CONDUCTIVITY SENSOR AND METHODS OF USE THEREOF

CROSS-REFERENCE TO RELATED APPLICATIONS

This application is a divisional of U.S. patent application Ser. No. 17/724,204 filed on Apr. 19, 2022, which is a divisional of U.S. patent application Ser. No. 16/120,224 filed on Sep. 1, 2018 and entitled "FLUIDIC CHANNELS INCLUDING CONDUCTIVITY SENSOR AND METHODS OF USE THEREOF," which claims the benefit of U.S. Provisional Patent Application No. 62/694,621 filed on Jul. 6, 2018, U.S. Provisional Patent Application No. 62/694,594 filed on Jul. 6, 2018, and U.S. Provisional Patent Application No. 62/694,599 filed on Jul. 6, 2018, the disclosures of which are incorporated herein by reference thereto.

BACKGROUND

There are numerous instruments and measurement techniques for diagnostic testing of materials related to medical, veterinary medical, environmental, biohazard, bioterrorism, agricultural commodity, and food safety. Diagnostic testing traditionally requires long response times to obtain meaningful data, involves expensive remote or cumbersome laboratory equipment, requires large sample size, utilizes multiple reagents, demands highly trained users, and can involve significant direct and indirect costs. For example, in both the human and veterinary diagnostic markets, most tests require that a sample be collected from a patient and then sent to a laboratory, where the results are not available for several hours or days. As a result, the caregiver must wait to treat the patient.

Point of use (or point of care when discussing human or veterinary medicine) solutions for diagnostic testing and analysis, although capable of solving most of the noted drawbacks, remain somewhat limited. Even some of the point of use solutions that are available are limited in sensitivity and reproducibility compared to in laboratory testing. There is also often significant direct costs to a user as there can be separate systems for each point of use test that is available.

SUMMARY

Disclosed herein are devices that includes a first portion, the first portion including at least one fluid channel; a fluid actuator; an analysis sensor disposed within the fluid channel; a conductivity sensor disposed within the fluid channel; and an introducer; a second portion, the second portion comprising: at least one well, the well containing at least one material, wherein one of the first or second portion is moveable with respect to the other, wherein the introducer is configured to obtain at least a portion of the material from the at least one well and deliver it to the fluid channel, and wherein the fluid actuator is configured to move at least a portion of the material in the fluid channel.

Also disclosed are methods of using systems, the system including: a first portion, the first portion including: at least one fluid channel; a fluid actuator; an analysis sensor disposed within the fluid channel; a conductivity sensor disposed within the fluid channel; and an introducer; a second portion, the second portion including: at least one well, the well containing at least one material, wherein one of the first or second portion is moveable with respect to the other, wherein the introducer is configured to obtain at least a portion of the material from the at least one well and deliver it to the fluid channel, and wherein the fluid actuator is configured to move at least a portion of the material in the fluid channel, the method including: monitoring a resistance of the conductivity sensor; moving a liquid within the fluidic channel; and monitoring a change in the resistance of the conductivity sensor.

Also disclosed are methods of utilizing systems, the system including: a first portion, the first portion including: at least one fluid channel; a fluid actuator; an analysis sensor disposed within the fluid channel; a conductivity sensor disposed within the fluid channel; and an introducer; a second portion, the second portion including: at least one well, the well containing at least one material, wherein one of the first or second portion is moveable with respect to the other, wherein the introducer is configured to obtain at least a portion of the material from the at least one well and deliver it to the fluid channel, and wherein the fluid actuator is configured to move at least a portion of the material in the fluid channel, the method including: monitoring a resistance at the conductivity sensor; starting a flow of liquid within the fluidic channel, the flow having a flow rate; determining the time that the resistance was maintained at a substantially constant value; and determining the volume of fluid in at least a portion of the fluidic channel based on at least the time that the resistance was maintained at a substantially constant value and the flow rate of the liquid.

These and various other features will be apparent from a reading of the following detailed description and related drawings.

BRIEF DESCRIPTION OF THE DRAWINGS

FIG. 1 is a schematic diagram illustrating an illustrative sensor assembly.

DETAILED DESCRIPTION

In the following detailed description several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

Disclosed devices include a conductivity sensor that can determine the conductivity of at least a portion of the fluid within the device it is located in. The conductivity can be utilized for various purposes.

Disclosed herein is an assembly. In some embodiments, assemblies can include a first portion and a second portion. The first and second portions can be configured to be assembled together to form an assembly. The first and second portions can be assembled together by a manufacturer, an assembler, an end-user, or any combination thereof. The assembly of the two portions can be facilitated by the shape of the two portions, components of at least one of the two portions that are designed to facilitate assembly, or some combination thereof. The two portions can be made of the same material(s) or different materials. In some embodiments the first portion and the second portion can be made of different materials, which because of the different purposes of the two portions, may be useful. The two portions of the assembly can be manufactured separately, in the same or different facilities; and/or can be packaged and/or sold separately or together.

At least one of the first and second portions is moveable with respect to the other. This implies that after the first and second portion are assembled to form the assembly, one portion is moveable with respect to the other. The portion that is moveable with respect to the other can be moveable in one or more directions or dimensions. Movement of one portion with respect to the other may offer advantages in that wells in the second portion (discussed below) can be randomly accessed by the first portion. The ability to randomly access the wells in the second portion can allow a large breadth of protocols to be accomplished without altering the configuration of the assembly itself. Other possible advantages provided by the movability of one portion with respect to the other portion are discussed throughout this disclosure.

FIG. 1 illustrates an illustrative embodiment of an assembly. This illustrative assembly 100 includes a first portion 110 and a second portion 120. This particular illustrative assembly 100 is configured to be assembled in a way that positions the second portion 120 below the first portion 110 in the z direction. In some embodiments, the second portion 120 is moveable with respect to the first portion 110. The second portion being moveable with respect to the first portion can imply that the second portion can move in at least one dimension (x, y, or z) with respect to the first portion, which is stationary. In some embodiments, the second portion can move along a straight line with respect to the first portion (for example, along the x dimension). The embodiment depicted in FIG. 1 shows such movement, with the second portion 120 moving in the x direction (as indicated by the arrow designated m). In some embodiments, the second portion can move along a straight line with respect to the first portion (for example along the x dimension) and can move up and down with respect to the first portion (for example along the z dimension). Such movement could be seen in the assembly 100 if the second portion 120 also moved in the z dimension.

First Portion

The first portion can include at least one fluidic pathway, a fluid actuator, and an introducer. Fluidic pathways can also be described as including a fluid channel. The illustrative first portion 110 illustrated in FIG. 1 includes a fluid channel 112, a fluid actuator 114, and an introducer 116. Generally, the fluid channel 112, the fluid actuator 114, and the introducer 116 are in fluid communication with one another. It can also be described that the fluid actuator 114, the introducer 116, and the fluid channel 112 are within, on, or are part of the fluidic pathway.

The fluidic pathway can have various configurations, and the examples depicted herein serve only as illustrative configurations. In some embodiments, the fluidic pathway does not include portions of the device that obtain the sample. In some embodiments, the fluidic pathway begins after a sample is contained in a well of the second portion. The fluidic pathway can be described as a transit path for fluids in the assembly. The fluidic pathway need not be fluidly connected at all times. For example, the fluidic pathway can include a portion of the device that can be (based may be moved into or out of the fluid pathway, by for example moving one portion with respect to another portion. The fluidic pathway can also be described as including any portion of the device accessible by the introducer, any portion of the device fluidly connected with any portion of the device accessible by the introducer, or some combination thereof. The fluidic pathway need not include only an actual volume that is connected. In some embodiments, a fluidic pathway can be entirely housed on a first portion, entirely housed on a second portion, or at least one portion of a fluidic pathway can exist on a first and at least one portion of a fluidic pathway can exist on a second portion. In some embodiments, a fluidic pathway can be one that is connected at all times and in some embodiments, one or more than one portion of a fluidic pathway can be at some times disconnected from the remainder of the fluidic pathway. In some embodiments, a fluidic pathway can include a fluid channel. In some embodiments, such a fluid channel can be a volume that is connected at all times. In some embodiments, such a fluid channel can be entirely housed on the first portion of an assembly. In some embodiments, such a fluid channel can be entirely housed on the first portion of an assembly can be a volume that is statically connected at all times. A fluid channel can refer to a physical channel on a first portion of an assembly.

In some embodiments, the fluidic pathway does not include valves. In some embodiments, the fluid channel does not include valves. In some embodiments, fluid can flow in either direction in the fluidic pathway (or in the fluid channel) even though there are no valves. Bi-directional flow is possible, even though there may be no valves in the fluidic pathway (or the fluid channel) because of the ability to randomly access wells (for example an empty well) in the second portion. More specifically, two directional flow can be accomplished by depositing liquid (in some embodiments all the liquid) in the fluidic pathway (or the fluid channel) in an empty well on the second portion by flowing the fluid in a first direction and then retrieving that liquid from that well and directing it in the fluidic pathway by flowing the fluid in a second direction (opposite to the first direction). Accomplishing two way flow without the use of any valves can make disclosed assemblies more cost effective to manufacture and less prone to issues that may accompany the use of valves.

Fluidic pathways (and therefore fluid channels that are part of a fluidic pathway) can have access to a sample introduction pathway as well. The sample introduction pathway and the fluidic pathway need not be entirely located on or in the same portion. The sample introduction pathway can include one or more than one component that can function to get a sample into a well. The sample introduction pathway can be described as a transit path for the sample before it is in a well. The sample introduction pathway need not be fluidly connected at all times. For example, the sample introduction pathway can include a portion of the device that can be (based on for example movement of one portion with respect to the other portion) moved into or out of the sample introduction pathway.

The sample introduction pathway can include, for example a sample introduction chamber and one or more than one component to get a sample from the sample introduction chamber to a well (on the second portion, discussed below). In some embodiments the sample introduction pathway can include one or more than one irreversible valve. A valve or valves that may be in the sample introduction pathway can also be described as not including moving parts. In some embodiments the sample introduction chamber can be located on or in the first portion. The sample introduction pathway can for example include a valve(s), a filter(s), or some combination thereof. In some embodiments the sample introduction pathway can utilize the introducer portion of the first portion. In some embodiments the sample can be moved from a sample introduction chamber to a sample well on the second portion.

In some embodiments, a sample introduction pathway can be configured to introduce sample directly into a fluidic pathway or a fluid channel that is part of a fluidic pathway. In such embodiments, the sample introduction pathway would be configured to deposit a sample into the fluidic pathway without first depositing it into a sample well. Such configurations could be especially useful or applicable to instances where the sample size is relatively small. In some embodiments, such configurations could be utilized for sample sizes of not greater than 100 µL, for example. An example of such a sample could include a quantity of blood obtained via a finger prick.

FIG. 1 shows a fluid channel 112 that is part of the fluidic pathway. The fluid channel 112 can be formed (i.e., top, bottom and sides) from more than one component or piece of the first portion. In some embodiments, the fluid channel 112 does not contain any fluid valves. Illustrative fluid channels can be described by their volumes, either by their total volumes or by the volume both before and after the analysis sensor. In some embodiments, illustrative fluid channels can have volumes of 10 µL to 1000 µL in the region before the analysis sensor and 10 µL to 1000 µL in the region after the analysis sensor. In some embodiments, illustrative fluid channels can have volumes of 50 µL to 250 µL in the region before the analysis sensor and 50 µL to 250 µL in the region after the analysis sensor. In some embodiments, illustrative fluid channels can have volumes of 75 µL to 200 µL in the region before the analysis sensor and 75 µL to 200 µL in the region after the analysis sensor. In some embodiments, illustrative fluid channels can have volumes of 100 µL to 175 µL in the region before the analysis sensor and 100 µL to 175 µL in the region after the analysis sensor. It should also be understood that the volumes before and after the analysis sensor need not be the same.

The first portion also includes a fluid actuator 114. Although fluid actuator 114 is depicted as being at one end of the fluid channel 112, it should be understood that a fluid actuator could be located at any point along the fluid channel 112, could be located at multiple points along the fluid channel 112, and/or could have multiple components at multiple points along the fluid channel 112. The fluid actuator 114 functions to move fluid along the fluid channel 112. It can also be described that the fluid actuator 114 functions to move fluid along, into, out of, within (or any combination thereof) the fluid channel 112.

The fluid actuator 114 can be as simple as a port or as complex as a pump or diaphragm. In some embodiments, the fluid actuator 114 can be a port at the end of the fluid channel 112 (for example such as that depicted in FIG. 1) that is in fluid communication with a pump located external to the first portion. In some embodiments, the fluid actuator 114 is a port that is in fluid communication with a pump that is located on or within an external instrument that is configured to control and/or manipulate the sensor assembly. In some embodiments, the fluid actuator 114 can be a port that is in fluid communication with an entire fluidic control system. Illustrative fluidic control systems can include a pump(s), diaphragm(s), valve(s), further fluid channel(s), reservoir(s), or some combination thereof. In some embodiments, at least portions of the illustrative fluidic control system can be located on or within an external instrument, the first portion of the sensor assembly, the second portion of the sensor assembly, or some combination thereof. In some embodiments, the fluid actuator 114 can include a diaphragm that is in fluid communication with some portion of a fluidic control system.

The first portion also includes an introducer 116. The introducer 116 is on, within, or fluidly attached to the fluid channel 112 and functions to access the wells of the second portion (discussed below). The function of the introducer 116 can also be described as being configured to obtain at least a portion of the contents of at least one well on the second portion. The introducer 116 can be described as being able to both puncture sealed wells of the second portion and access and obtain at least a portion of the material in the well. The introducer 116 can be actuated by an external instrument in order to access the wells. Such actuation can include movement in one or more than one dimension. For example, in the example depicted in FIG. 1, movement of the introducer 116 in the z direction could afford access to at least one well on the second portion.

In some embodiments, the introducer 116 can also be configured to introduce air into a well it has accessed. This may allow the introducer 116 to more reliably obtain material from the wells. This optional function of the introducer 116 can be realized by the particular design of the tip of the introducer, by puncturing the seal to the well at two (instead of one) points simultaneously, at different times in a specified order, or by combinations thereof. In some embodiments, the introducer 116 can be similar in shape and configuration to a pipette tip.

The introducer 116 can also be configured to both extract material from a well of the second portion and introduce material into a well of the second portion. In such embodiments, the external instrument, in some embodiments through control of a pump for example, can control whether the introducer 116 is extracting or introducing material from or into the well. Introducing material into a well can allow for storage of materials, while not requiring a user to have concerns about liquids spilling out of a used sensor assembly. Introducing material into a well can also provide a method of mixing. Introducing material into a well can also provide a method of storing an intermediate composition while another step of a protocol is being carried out.

In some embodiments, the first portion 110 can also include an analysis sensor 118. An analysis sensor in a first portion can be any type of sensor, for example it could be an optical sensor (using for example chemiluminescence or fluorescence), an electrochemical sensor, or a resonant sensor. In some embodiments, the analysis sensor 118 can include at least one resonator sensor. Examples of such sensors can include bulk acoustic wave (BAW) sensors and thin film bulk acoustic resonator (TFBAR) sensor. Both BAW and TFBAR sensors include a piezoelectric layer, or piezoelectric substrate, and input and output transducer. Both BAW and TFBAR sensors are small sensors making the technology particularly suitable for use in handheld or portable devices.

In some embodiments, the analysis sensor 118 can be within or form part of the fluidic pathway. More specifically, in some embodiments, the analysis sensor 118 can be within or form part of the fluid channel. For example, a portion of the fluidic pathway can be configured to exist within or form part of the fluidic pathway so that fluid in the fluidic pathway flows over the analysis sensor. In some embodiments, the fluid in the fluidic pathway can travel completely around the sensor, and in other embodiments, the fluid in the fluidic pathway can travel around less than all surfaces of the analysis sensor. In some embodiments, the fluid in the fluidic pathway can travel across the active region of the analysis sensor. In some embodiments, the fluid in the fluidic pathway can flow over the piezoelectric layer of the analysis sensor, which is coated with binding sites for an analyte of interest.

The analysis sensor can be any type of sensor. In some embodiments the analysis sensor can be an optical sensor (for example a chemiluminescent sensor or a fluorescent sensor) or a resonant sensor, for example. In some embodiments the analysis sensor can be a resonant sensor, such as a BAW sensor.

Disclosed devices include a conductivity sensor disposed within the fluidic channel. The conductivity sensor can generally include at least two electrodes. In some embodiments, the electrodes are made of a material that will not be reactive with the fluid (e.g., sample, reagents, or sample and reagents in combination) that will be located within the fluidic channel. In some embodiments, the electrodes can be made of a substantially chemically inert material. In some embodiments, the electrodes can be made of gold for example.

The at least two electrodes can have the voltage and current characteristics configured in order to measure the resistance of the fluid within the fluidic channel. The at least two electrodes can be employed with alternating current (AC), direct current (DC), or a combination thereof. In some embodiments, AC current can be utilized as it will prevent or at least minimize hydrolysis at the surface of the electrodes. In some embodiments, relatively low current are utilized in order to avoid substantial joule heating of the fluid within the fluidic channel.

The conductivity sensor can be in communication, for example electrical communication, with a processor that can obtain signals from the sensor and utilize the signal for various purposes. Additionally, or alternatively, the conductivity sensor can be controlled by a processor, e.g., the processor can activate the conductivity sensor at various times, for various lengths of time, or combinations thereof.

The conductivity sensor can be located upstream of the analysis sensor or downstream of the analysis sensor. In some embodiments, the conductivity sensor can be located upstream of the analysis sensor. In embodiments where the conductivity sensor is located upstream of the analysis sensor, the conductivity sensor can be utilized to meter sample, reagents, both sample and reagents or mixtures thereof.

When the conductivity sensor (e.g., the two electrodes) is exposed to air, the sensor will measure a high resistance. When contacted with a liquid sample containing ions the resistance changes (lowers) according to the concentration level of ions in the liquid. The time when the change of resistance occurs indicates when the liquid sample is in contact with both electrodes. The exact point when the liquid is in contact with both electrodes of the conductivity sensor can be utilized for various purposes in a disclosed system. Disclosed methods can therefore include steps of monitoring a conductivity sensor located within the fluidic channel, moving liquid (or starting the flow of liquid) within the fluidic channel, and monitoring a decrease in resistance at the conductivity channel. Various steps can optionally be carried out in addition to the three steps above depending on the purpose and/or goal of a disclosed method.

In some embodiments, a system including a conductivity sensor can be utilized to meter fluids. In a fluid metering application, the fluid can be stopped consistently when the resistance change is detected. Depending on the fluid driving mechanism, fluid could be stopped immediately when the resistance lowers. This is accomplished by stopping the driving mechanism very shortly or even immediately after the resistance changes. Disclosed methods can therefore include steps of monitoring a conductivity sensor located within the fluidic channel, starting the flow of liquid within the fluidic channel, monitoring a decrease in resistance at the conductivity sensor, and stopping the flow of the liquid in the fluidic channel.

In some embodiments, pressure that has built up in the system to drive the fluid could make stopping the fluid quickly somewhat difficult. In this case, slower fluid flow would lower the pressure build up and allow the fluid to stop more quickly. The problem may worsen as the sample viscosity increases since a higher pressure is needed for an equivalent flow rate. However, slow flow may not be desirable, especially in rapid point of care testing where time to meter samples could add significantly to the time necessary to obtain the result.

In some embodiments, there may be two alternatives for allowing fast metering. Using a fast forward flow until the resistance lowers and then stopping the pump where the fluid overshoots the electrodes. Reversing flow slowly until a high resistance is measured and stopping the pump. Some such disclosed methods can therefore include steps of monitoring a conductivity sensor located within the fluidic channel, starting the flow of liquid within the fluidic channel in a first direction at a first flow rate, monitoring a decrease in resistance at the conductivity channel, stopping the flow of the liquid in the fluidic channel, and reversing the flow of liquid in the fluidic channel at a second flow rate where the first flow rate is faster than the second flow rate and then stopping the flow of fluid. Methods such as this may only see modest gains in reducing the metering time.

A second type of method for allowing fast metering includes moving the fluid fast toward the electrodes and upon the resistance change the pump is stopped and vented. This removes the residual pressure buildup in the fluid channels quickly and allows the fluid to stop quickly. Some such disclosed methods can therefore include steps of monitoring a conductivity sensor located within the fluidic channel, starting the flow of liquid within the fluidic channel in a first direction at a first flow rate, monitoring a decrease in resistance at the conductivity channel, stopping the flow of the liquid in the fluidic channel, and venting the fluidic channel.

In some embodiments, a system including a conductivity sensor can be utilized to estimate the total volume of a slug of fluid in a portion of the fluidic channel. When applying a volumetric metering method such as described above (or another), typically the presence of fluid is guaranteed at the meter stop (conductivity sensor, hydrophobic vent or other) and an assumption is made that fluid is continuous in the meter channel.

A conductivity sensor can be used to confirm that the fluid is continuous in the meter channel and estimate the total volume. The metered fluid slug can be driven past the conductivity sensor and the volume of the fluid slug can be estimated by the fluid driving method used. For example a positive displacement pump can be used to drive the fluid at a specific flow rate. The total time that liquid is observed on the conductivity sensor can then be used to estimate the volume of fluid based on the flow rate. Some such disclosed methods can therefore include steps of monitoring a conductivity sensor located within the fluidic channel, starting the flow of liquid within the fluidic channel, determining the time that the resistance was maintained at a substantially constant value and determining the volume of fluid in at least a portion of the fluidic channel based on the time that the resistance was maintained at a substantially constant value and the flow rate of the liquid.

Pressure data could also be used to improve the estimate by compensating for the actual fluid flow rate when the fluid flow rate is not in steady state. Some such disclosed methods can therefore include steps of monitoring a conductivity sensor located within the fluidic channel, monitoring the pressure within the fluidic channel, starting the flow of liquid within the fluidic channel, determining the time that the resistance was maintained at a substantially constant value and determining the volume of fluid in at least a portion of the fluidic channel based on the time that the resistance was maintained at a substantially constant value, the flow rate of the liquid, and the pressure within the fluidic channel.

Different pumping methods may dictate different methods for how the fluid volume is estimated. Such estimates of sample volume can be used to positively confirm the presence of adequate sample and identify occurrences of too little sample. Meter methods alone (such as described above) may only identify no sample if timeout errors in the metering method are employed.

Disclosed systems can also be utilized to control mixing of a sample and reagents, or any combination thereof. Typically metered fluids need to be mixed with additional fluids to perform reactions. The final concentration(s) in the mixture is important to the precision of the analytical result reported by a test. One way to achieve an accurate and precise concentration in the final mixture of two reagents, for example, is to meter reagent one from an excess and add it to an already accurate/precise volume (at time of manufacture) of reagent two. In some such methods, any of the above methods of determining a volume of liquid in a fluidic channel can be combined with a step of adding the volume of liquid to a known volume of a second liquid. In some methods, the first liquid can be a sample and the second liquid can be a reagent, the first liquid can be a reagent and the second liquid can be a sample, the first liquid can be a reagent and the second liquid can be a reagent, the first liquid can be a sample and the second liquid can be a diluent for the sample, or any combination thereof. In some embodiments, reagent can be metered more than once into an already accurate/precise volume of reagent two.

A potential problem with this approach is that volumetric metering methods in a fluidic device are dependent on accurate channel geometries as well as assembly tolerances. Injection molded parts produced from the same cavity are consistent enough to achieve good precision using this method. However, parts produced from multiple cavities may not be consistent enough due to tool variations.

Alternatively one can achieve an accurate and precise concentration in the final mixture using a ratio-metric approach. Here, reagent one is metered from an excess (e.g., a method including monitoring a conductivity sensor located within the fluidic channel, starting the flow of liquid within the fluidic channel, monitoring a decrease in resistance at the conductivity channel, and stopping the flow of the liquid in the fluidic channel). Next reagent two is metered from an excess using the same metering method. The two metered volumes are then mixed. Now, a 1:1 mixture is achieved with accurate and precise concentration but the final volume could be considered inaccurate. If the accuracy of the total volume of the mixture is not important to the final test result, this method avoids the multi-cavity tool problem, with the added expense of two meter steps. It should be noted that the ratio is not limited to 1:1. For example the first liquid (and/or the second liquid) could be metered multiple times (a fixed volume meter apparatus) to achieve different mixture ratios. Variable volume meter methods certainly are not limited either.

The volume of the liquid in ratiometric methods, if it is necessary to be known, can be estimated using a number of factors, including for example, the fluid volume in the fluidic channel using the geometry of the channel, the pressure in the channel, the flow rate of the fluid, the fluidic resistance, the time the fluid was moved, or some combination thereof.

Second Portion

Disclosed assemblies also include a second portion. The second portion can include at least one well. FIG. 1 depicts an illustrative second portion 120 that includes a plurality of wells 122. Disclosed second portions of the assembly can include any number of wells. In some embodiments, a second portion can include at least one (1), at least three (3), or at least five (5) wells. In some embodiments, a second portion can include nine (9) wells with one being a sample well. The wells can be present in any configuration, linear (as depicted in FIG. 1, circular, or otherwise).

The wells within a second portion can be configured to contain the same or different volumes. In some embodiments, the wells can be of a size to contain at least 10 µL. In some embodiments, the wells can be of a size to contain from 50 µL to 150 µL, for example. In some embodiments, the wells can be of a size to contain about 100 µL for example. In some embodiments, the wells can have a total volume that is more than the quantity which they are designed to hold. For example, a well can have a total volume that is 200 μL in order to house a volume of 100 μL. The wells can have various configurations, including for example corners, flat bottoms, and round bottoms. The wells can have various shapes, for example, they can be cylindrical, or spherical, hexagonal, or otherwise.

Wells within a second portion can contain various materials or can be empty. In some embodiments, a second portion can include at least one well that is empty. In some embodiments a second portion can include at least one sample well. The sample well can generally be empty before the assembly is used. The sample well in such embodiments can be utilized to hold at least a portion of the sample transferred from a sample introduction chamber via the sample introduction pathway. In some embodiments, the sample well can include one or more than one materials, which the sample will be combined with upon introduction into the sample well.

Materials contained within wells can be liquid or solid. Materials contained within wells can also be referred to as reagents, diluents, wash solutions, buffer solutions, or other such terms. In some embodiments, material within a well can be a single material that is a liquid at room temperature, a solution containing more than one material, or a dispersion containing one material dispersed in another. In some embodiments, material within a well can be a solid. The material within an individual well can be independently selected with respect to materials in other wells. In some embodiments, the materials within a well are selected to carry out a particular testing protocol.

The second portion can also include a seal. Generally, the seal functions to contain the materials within the wells. In some embodiments, the seal can be a unitary element, while in some embodiments, the seal can be made up of more than one element. For example, with reference to FIG. 1, in some embodiments, a single element could cover all of the wells 122. While in some other embodiments, each well 122 could be covered by an individual element, with all of the elements making up the seal. The seal can be made of any material that can function to maintain the contents of the wells within the wells, but also allow the introducer access to the materials in the wells. Illustrative materials can include, for example, a foil, such as a metallic foil which can be sealed to the second portion (or portions thereof) via an adhesive or heat sealing; plastic films; or other such materials. In some embodiments, the seal is made of a metallic foil and covers the entirety of the second portion.

The second portion can also include a way of introducing a sample either directly or indirectly from a user. For example, in some embodiments, a second portion can include an empty well, whose seal can be pierced (if it is sealed) by a portion of a disclosed assembly or a user to introduce a sample to be tested by the sensor assembly. This well can be referred to as the sample well. In some embodiments, the sample well is not covered by the seal. In some embodiments where the sample is introduced directly to the second portion by a user it can be added to the sample well via a syringe, a pipette, or other similar instruments. In some embodiments, the sample can be added to a sample well via, for example a sample introduction pathway.

Uses

The devices, systems, and methods described herein may be employed to detect a target analyte in a sample. The devices may find use in numerous chemical, environmental, food safety, or medial applications. By way of example, a sample to be tested may be, or may be derived from blood, serum, plasma, cerebrospinal fluid, saliva, urine, and the like. Other test compositions that are not fluid compositions may be dissolved or suspended in an appropriate solution or solvent for analysis.

Non-limiting examples of target analytes include nucleic acids, proteins, peptides, antibodies, enzymes, carbohydrates, chemical compounds, or infectious species such as bacteria, fungi, protozoa, viruses, pesticides and the like. In certain applications, the target analyte is capable of binding more than one molecular recognition component.

The present disclosure is illustrated by the following examples. It is to be understood that the particular examples, assumptions, modeling, and procedures are to be interpreted broadly in accordance with the scope and spirit of the disclosure as set forth herein.

Thus, embodiments of FLUIDIC CHANNELS INCLUDING CONDUCTIVITY SENSOR AND METHODS OF USE THEREOF are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A method of regulating a fluid at a fluidic device, the method comprising:
   providing a first portion of the fluidic device comprising a fluidic channel;
   providing a second portion of the fluidic device, operatively coupled to and physically separate from the first portion, and comprising one or more wells;
   configuring the first and second portions to move relative to one another between a first position where the fluidic channel is fluidly coupled to at least one well of the one or more wells, and a second position away from the first position;
   moving a fluid from the at least one well to the fluidic channel;
   moving the fluid in the fluidic channel of the fluidic device in a first direction at a first flow rate; and
   changing the flow of the fluid when a change in resistance is measured at a sensor of the fluidic device.

2. The method of claim 1, wherein the step of moving the fluid in the fluidic channel of the fluidic device comprises starting the flow of liquid in the fluidic channel.

3. The method of claim 1, further comprising reversing the flow of fluid in the fluidic channel in a second direction at a second flow rate different than the first flow rate.

4. The method of claim 1, wherein the fluidic device comprises a fluidic actuator configured to move the fluid in the fluidic channel, and the second portion is configured to be moved in a linear direction under an introducer of the first portion.

5. The method of claim 1, wherein the sensor is a conductivity sensor, and is located upstream of an analysis sensor.

* * * * *